United States Patent [19]

Feasey et al.

[11] 3,949,002
[45] Apr. 6, 1976

[54] PROCESS FOR PRODUCING SULFONE CONTAINING THIOPHENOLS
[75] Inventors: Ronald George Feasey, Knebworth; John Brewster Rose, Letchworth, both of England
[73] Assignee: Imperial Chemical Industries Limited, London, England
[22] Filed: Oct. 29, 1971
[21] Appl. No.: 194,004

[52] U.S. Cl. ...... 260/609 D; 260/590 R; 260/465 R; 260/294.8 R; 260/206; 260/205; 260/591
[51] Int. Cl.²....................................... C07C 149/32
[58] Field of Search ................................ 260/609 D

[56] References Cited
UNITED STATES PATENTS
| | | | |
|---|---|---|---|
| 3,374,274 | 3/1968 | Spainhour | 260/609 D |
| 3,560,573 | 2/1971 | Blazejak et al. | 260/609 D |
| 3,607,877 | 10/1968 | Domenico | 260/609 D |

FOREIGN PATENTS OR APPLICATIONS
| | | | |
|---|---|---|---|
| 1,516,583 | 3/1968 | France | 260/609 D |

OTHER PUBLICATIONS
Chemische Berichte, Schultz et al., Beyschlag, pp. 743–752.

Primary Examiner—Lewis Gotts
Assistant Examiner—D. R. Phillips
Attorney, Agent, or Firm—Cushman, Darby & Cushman

[57] ABSTRACT

A method for the preparation of aromatic thiols which comprises reacting a benzenoid compound having at least one halogen atom activated by an inert electron-attracting group with an alkali metal disulphide in stoichiometric proportion of from 1.0 to 2.0 moles per gram atom of activated halogen to be replaced.

10 Claims, 1 Drawing Figure

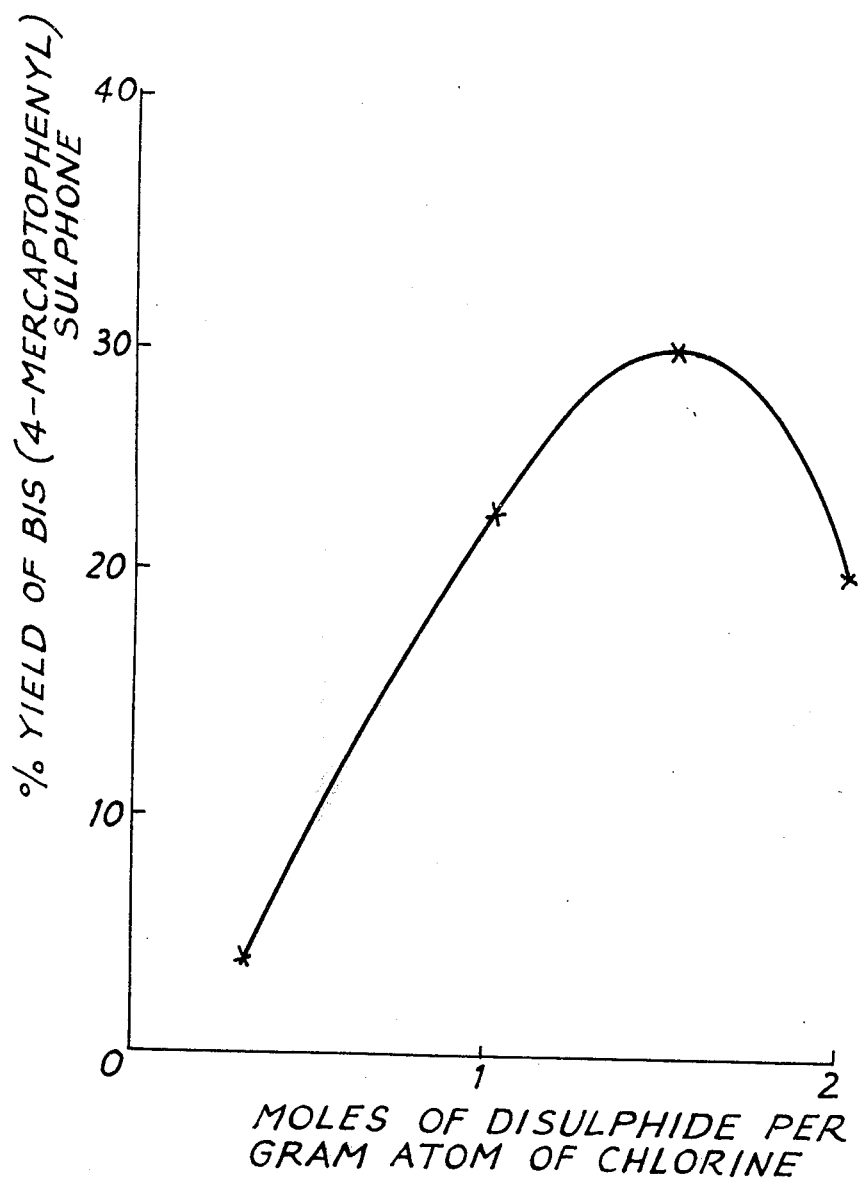

PROCESS FOR PRODUCING SULFONE CONTAINING THIOPHENOLS

This invention relates to organic thiols and in particular to aromatic thiols.

According to the present invention, a method is provided for the preparation of aromatic thiols which comprises reacting a benzenoid compound having at least one halogen atom activated by an inert electron-attracting group with an alkali metal disulphide in stoichiometric proportion of from 1.0 to 2.0 moles per gram atom of activated halogen to be replaced.

Any benzenoid compound having at least one halogen atom activated by at least one electron withdrawing group in at least one of the positions ortho or para to a halogen atom may be used in the process of the invention. Any electron withdrawing group may be used provided that it is inert to the reaction. More powerful electron withdrawing groups are preferred and preferably the aromatic ring containing the halogen atom to be replaced should not be substituted with any electron-donating groups, in any of the positions ortho or para to the halogenatom.

The activating group may be either a univalent group that activate one or more halogens on the same ring, e.g. a nitro group, phenylsulphone, or alkylsulphone, cyano, trifluoromethyl, nitroso, and hetero nitrogen as in pyridine, or a bivalent group which can activate displacement of halogen(s) on one (or two) rings, e.g. sulphone group (—SO$_2$—); carbonyl group (—CO—); vinyl group (—CH=CH—); sulphoxide group (—SO—); azo-group (—N=N—); saturated fluorocarbon group (—CF$_2$CF$_2$—); organic phosphine oxides [—PO(R)—]; where R is a hydrocarbon group, and the ethylidene group [—C(CX$_2$)—] where X can be hydrogen or halogen or which can activate halogens on the same ring such as with difluorobenzoquinone, 1,4- or 1,5- or 1,8-difluoroanthraquinone.

Examples of compounds containing a univalent activating group are:

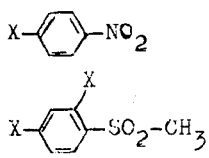

and of compounds containing a bivalent activating group are

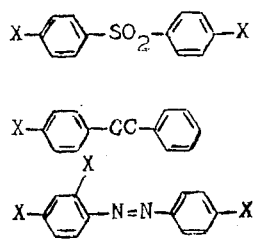

where X is a halogen atom.

The halogen atoms, X, are preferably chlorine atoms or bromine atoms. Bromine derivatives are relatively expensive although they resemble chlorine derivatives in performance. Iodine derivatives may also be used but fluorine derivatives are generally less suitable.

The alkali metal disulphide has essentially the molecular formula M$_2$S$_2$ where M is an alkali metal. Some or all of the alkali metal cation in the reagent may be replaced by an organic onium cation having a positively charged heteroatom (for example a quaternary ammonium cation such as tetramethylammonium) stable under the conditions of the reaction, and the term "alkali metal salt" as used herein is deemed to refer also to salts containing such onium cations. Preferably the alkali metal cation is sodium or potassium ammonium. The disulphide is conveniently prepared by reacting approximately a given gram atom of sulphur with the same moles of alkali metal sulphide.

The reaction of the invention is desirably carried out in the presence of a solvent which is preferably an alcohol, a glycol, or a glycol monoether, of which ethylene glycol is particularly preferred.

As with most chemical reactions, a compromise has to be reached between obtaining essentially a single product by performing the reaction at ambient temperature over a long period of time or carrying out the reaction at higher temperatures over a shorter reaction time with attendant risk of a multiplicity of products and product degradation. The reaction of the present invention may be carried out at temperatures between ambient and 200°C, preferably between 100° and 140°C.

The reaction is also carried out preferably in an inert atmosphere, e.g. nitrogen, so as to reduce the risk of oxidation of the thiol group and attendant risk of polymerisation.

In accordance with the method of the present invention, from 1.0 to 2.0 (preferably 1.3 to 1.7) moles of alkali metal disulphide are present for each gram atom of halogen to be replaced in the benzenoid compound if the yield of aromatic thiol is to be optimised. Hence if 1 mole of a dihalogenated benzenoid compound (in which both halogen atoms are activated) is reacted with 3 moles of alkali metal disulphide, 1 mole of bis-thiol will be produced; if 1 mole of a dihalo benzenoid compound is reacted with about 1.5 moles of alkali metal disulphide, then 1 mole of the halothiol of the benzenoid compound will be formed.

The thiol is conveniently extracted from the reaction mixture by acidification followed by filtration, washing of the precipitate and drying, preferably in an atmosphere of nitrogen at temperatures less than 80°C so as to minimise the risk of oxidation.

In a preferred embodiment of the method of the invention the crude precipitated thiol is extracted into an aqueous solution of an alkali metal sulphite and the solution filtered. The filtrate is then acidified to a pH of greater than 5 conveniently with mineral acid (e.g. hydrochloric acid) to precipitate thiol which can be filtered, washed and dried as described hereinbefore. The precipitate from the sulphite extraction is treated with warm aqueous alkali metal sulphide solution and the resulting solution filtered. This filtrate is acidified to about pH 1 with mineral acid to precipitate further quantities of crude thiol which can be filtered off and extracted into aqueous solution of alkali metal sulphite as before.

The thiols of the invention may be used in the preparation of pharmaceutical products and in particular bisthiols may be used in the preparation of polymeric materials such as for example those described in U.S. Pat. No. 3,432,468, German Pat. No. 1,938,806 and Netherlands Pat. No. 6,903,070 and halothiols by a method similar to that described in British patent specifications 1,153,035 and 1,177,183.

The invention is illustrated by the following examples.

EXAMPLE 1

Sodium sulphide nonahydrate ($Na_2S.9H_2O$; 864.7 g; 3.6 moles) and elemental sulphur (115.2 g; 3.6 g atoms) were dissolved in ethylene glycol (1800 cm$^3$) in a roundbottomed flask fitted with a stirrer, condenser, and nitrogen inlet. Bis-(4-chlorophenyl)sulphone (344.6 g; 1.2 moles) were added and the mixture stirred and heated at 130°C for 20 hours under an atmosphere of nitrogen. The dichloride had completely dissolved after 2.5 hours.

The dark brown reaction mixture was cooled, diluted with water (5 dm$^3$) and the solution was acidified to pH 1 with hydrochloric acid. The pale yellow precipitate was filtered off and washed well with water.

The precipitate was digested for 3 hours at 90°–100°C with a solution containing sodium sulphite heptahydrate ($Na_2SO_3.7H_2O$; 1815.8 g; 7.2 moles) in 3 dm$^3$ of water. The mixture was allowed to cool to room temperature and the insoluble material filtered off and washed with water. The pale yellow aqueous sulphite extract and washings were acidified, with stirring, to pH 5.5 with hydrochloric acid, and the white granular product, bis-(4-mercaptophenyl) sulphone (89 g) was filtered off, washed with water, and dried at 70°C under nitrogen.

The sulphite insoluble material was dissolved in 2 liters of aqueous sodium sulphide solution (2 dm$^3$ containing 350 g of $Na_2S.9H_2O$) at 60°C. The solution was filtered to remove impurities, and acidified to pH 1. The precipitate was filtered off, washed with water and digested with aqueous sodium sulphite solution (containing 400 g of $Na_2SO_3.7H_2O$) as described above. A further 54 g of bis-(4-mercaptophenyl) sulphone were isolated by acidifying the sulphite extract.

The procedure of dissolving the sulphite-insoluble material in aqueous sulphide solution, acidifying, and digesting with aqueous sulphite solution, was repeated twice - i.e. four separate crops of bis-(4-mercaptophenyl) sulphone were obtained. For the third cycle, 250 g of sulphide and 300 g of sulphite were used, and for the fourth, 150 g of sulphide and 200 g of sulphite. The third and fourth cycle yields of bis-(4-mercaptophenyl) sulphone were 62 g and 32 g respectively.

The total yield of bis-(4-mercaptophenyl)sulphone was 237 g (70% based on bis-(4-chlorophenyl)sulphone and had melting point of 138°–140°C.

EXAMPLE 2

A series of experiments were carried out according to the procedure of Example 1, using varying amounts of sodium disulphide, in order to determine the optimum ratio of moles of disulphide per g atom of chlorine. The results in Table 1 show the % yield of bis-(4-mercaptophenyl)sulphone after a standard wash with sodium sulphite solution as described in Example 1. (i.e. % yield after 1st cycle).

TABLE 1

| Moles of disulphide per g.atom chlorine | % yield of bis-(4-mercaptophenyl) sulphone |
| --- | --- |
| 0.33 | 4 |
| 1.0 | 23 |
| 1.5 | 30 |
| 2.0 | 20 |

TABLE 1-continued

These results are presented in FIG. 1 and show that the optimum yield of bis-(4-mercaptophenyl)sulphone is obtained when 1.5 moles of disulphide per g atom of chlorine are used.

EXAMPLE 3

Sodium sulphide (60%; $Na_2S.3H_2O$; 465 g; 3.58 mole) and elemental sulphur (114.6 g; 3.58 mole) were dissolved in ethylene glycol (2400 cm$^3$) in a round-bottomed flask equipped with a stirrer, condenser, and nitrogen inlet. Bis-(4-chlorophenyl)ketone (300 g; 1.19 mole) was added and the mixture stirred and heated at 130°C for 4 hours.

The dark brown reaction mixture was cooled, diluted with water (6 dm$^3$) and the solution acidified to pH 1 with hydrochloric acid. The pale yellow precipitate was filtered off and washed well with water.

The precipitate was digested for 2 hours at 80°C with a solution containing sodium sulphite heptahydrate ($Na_2SO_3.7H_2O$; 1804 g; 7.16 mole) in 3 dm$^3$ of water. The mixture was allowed to cool to room temperature and the insoluble material filtered off and washed with water. The yellow aqueous sulphite extract and washings were acidified, with stirring to pH 5.5 with hydrochloric acid, and the pale yellow granular product, bis-(4-mercaptophenyl) ketone (80 g) was filtered off, washed with water, and dried at 70°C under vacuum.

The sulphite insoluble material was dissolved in aqueous sodium sulphide solution (2 dm$^3$ containing 400 g; 3.1 mole of 60% $Na_2S$) at 60°C. The solution was filtered to remove impurities and acidified to pH 1. The precipitate was filtered off, washed with water and digested with aqueous sodium sulphite solution (1562 g; 6.2 mole of $Na_2SO_3.7H_2O$) as described above. A further 70 g of bis-(4-mercaptophenyl)ketone was isolated by acidifying the sulphite extract.

The procedure of dissolving the sulphite-insoluble material in aqueous sulphide solution, acidifying, and digesting with aqueous sulphite solution, was repeated twice — i.e. four separate crops were obtained.

Table 2 illustrates the yields of bis-thiol obtained in each cycle together with amount of reagent.

TABLE 2

| | $Na_2S$ | $Na_2SO_3$ | Bis-thiol |
| --- | --- | --- | --- |
| Reaction mixture | 465 g (3.58 mole) | 1804 g (7.16 mole) | 80 g |
| 1st Cycle | 400 g (3.1 mole) | 1562 g (6.2 mole) | 70 g |
| 2nd Cycle | 280 g (2.15 mole) | 1084 g (4.3 mole) | 40 g |
| 3rd Cycle | 180 g (1.38 mole) | 700 g (2.7 mole) | 20 g |

The total yield of bis-(4-mercaptophenyl)ketone was 237 g [70% based on bis-(4-chlorophenyl)ketone] and the product on recrystallisation from ethanol had a melting point 176°–177°C.

EXAMPLE 4

Sodium sulphide (60% $Na_2S$; 26.0 g; 0.2 mole) and elemental sulphur (6.4 g; 0.2 mole) were dissolved in ethylene glycol (300 cm$^3$) in a round-bottomed flask equipped with a stirrer, condenser and nitrogen inlet. Bis-(4-chlorophenyl)ketone (65.2 g; 0.26 mole) was added and the mixture stirred and heated at 120°C for 4 hours under a nitrogen atmosphere.

The reaction mixture was cooled and the precipitated solid (unreacted bis-(4-chlorophenyl)ketone; 35 g) filtered off. The filtrate was diluted with water and acidified with hydrochloric acid. The precipitate was filtered off, washed with water and digested with aqueous sodium sulphite heptahydrate ($Na_2SO_3.7H_2O$; 100 g; 0.4 mole) at 80°C for one hour. The solid was filtered off and washed with water. The sulphite insoluble material was treated with aqueous sodium hydroxide solution (30 g; 0.85 mole in 200 cm³ of water) at 60°C for two hours. The cooled sodium hydroxide extract was filtered and the filtrate acidified with hydrochloric acid. The white precipitate was filtered off, washed with water and recrystallised from degassed ethanol and found to have infra-red and nuclear magnetic resonance spectra consistent with its being 4-chloro-4'-mercaptobenzophenone.

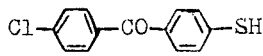

The yield of 4-chloro-4'-mercaptobenzophenone was 20 g [67% based on 30.2 g of bis-(4-chlorophenyl)sulphone].

EXAMPLE 5

A solution of sodium sulphide nonahydrate (35 g; 0.144 mole) and sulphur (4.69 g; 0.146 mole) in a mixture of water (100 cm³) and sulpholane (50 cm³) was slowly added to a stirred solution at less than 120°C of 4,4'-dichlorodiphenyl sulphone (28.7 g; 0.100 mole) in sulpholane (75 cm³), contained in a round-bottom flask fitted with a nitrogen inlet, a still head and a stirrer. The resulting solution was stirred for 2 hours under reflux. A solution of sodium hydroxide (8.0 g; 0.20 mole) in a mixture of water (50 cm³) and sulpholane (50 cm³) was added slowly to the reaction mixture which was stirred at 120°C for a further 2 hours. The resulting solution was cooled, poured on to ice and the clear solution obtained was acidified with concentrated hydrochloric acid. A solid precipitated which was extracted with two portions (ca. 250 cm³) of aqueous potassium hydroxide solution (4N). The combined alkaline extracts were acidified with concentrated hydrochloric acid and the precipitate was extracted into chloroform. The chloroform solution was dried over sodium sulphate and evaporated to yield a residue whose nuclear magnetic resonance, infra-red and mass spectra were consistent with the structure

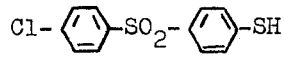

We claim:
1. A method for the preparation of aromatic thiols which comprises reacting in an inert solvent the corresponding aromatic halide having the halogen atom activated by an inert electron-attracting group attached to the same aromatic ring as the halogen atom and ortho or para thereto, wherein said electron-attracting group is —$SO_2$—, with an alkali metal disulphide in stoichiometric proportion of from 1.0 to 2.0 moles per gram atom of activated halogen to be replaced and then acidifying the reaction mixture.

2. A method according to claim 1 in which the alkali metal disulphide is present in stoichiometric proportion of from 1.3 to 1.7 moles per gram atom of activated halogen to be replaced.

3. A method according to claim 1 in which the aromatic thiol is extracted from the acidified reaction mixture which comprises filtering off precipitated crude thiol, digesting the crude thiol with an aqueous solution of alkali metal sulphite, filtering, and acidifying the filtered alkali metal sulphite solution to a pH of not less than 5 to thereby precipitate the thiol.

4. A method according to claim 3, which includes the further steps of digesting the solid residue obtained on filtering the alkali metal sulphite solution with an aqueous alkali metal sulphide solution to form a solution, acidifying this solution to precipitate a further quantity of crude thiol and then digesting this further quantity of crude thiol with an aqueous solution of an alkali metal sulphite, filtering, and acidifying the filtered alkali metal sulphite solution to a pH of not less than 5, thereby precipitating a further quantity of the thiol.

5. The process of claim 1 wherein the aromatic halide is bis-(4-chlorophenyl)sulphone and the thiol product is bis-(4-mercaptophenyl)sulphone.

6. The process of claim 1 wherein the aromatic halide is 4,4'-dichlorodiphenyl sulphone and the thiol product is 4-chloro-4'-mercaptophenyl sulphone.

7. Bis-(4-mercaptophenyl) ketone.

8. 4-Chloro-4'-mercaptobenzophenone.

9. 4-Chloro-4'-mercaptophenylsulphone.

10. A method according to claim 1 in which the aromatic halide has two activated halogen atoms.

* * * * *

UNITED STATES PATENT OFFICE
CERTIFICATE OF CORRECTION

Patent No. 3,949,002            Dated April 6, 1976

Inventor(s) Ronald George FEASEY and John Brewster ROSE

It is certified that error appears in the above-identified patent and that said Letters Patent are hereby corrected as shown below:

IN THE HEADING

After "Appln. No.: 194,004" insert --Claims priority, Applications Great Britain...November 13, 1970, No. 54131/70 and September 13, 1971, No. 42538/71--

IN THE SPECIFICATION

Column 2, line 10, after "potassium" insert --or--

IN THE CLAIMS

Delete claims 7 and 8.

Signed and Sealed this

Tenth Day of August 1976

[SEAL]

Attest:

RUTH C. MASON
Attesting Officer

C. MARSHALL DANN
Commissioner of Patents and Trademarks